US00PP26570P2

(12) United States Plant Patent
Kordes

(10) Patent No.: US PP26,570 P2
(45) Date of Patent: Apr. 5, 2016

(54) GRANDIFLORA ROSE PLANT NAMED 'KORFRE0005'

(50) Latin Name: *Rosa hybrida*
Varietal Denomination: KORfre0005

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes Sohne Rosenschulen GmbH & Co KG, Offenseth-Sparrieshoop (DE)

( * ) Notice: Subject to any disclaimer, the term of this patent is extended or adjusted under 35 U.S.C. 154(b) by 112 days.

(21) Appl. No.: 14/121,060

(22) Filed: Jul. 25, 2014

(51) Int. Cl.
*A01H 5/00* (2006.01)

(52) U.S. Cl.
USPC ..... Plt./130

(58) Field of Classification Search
USPC ..... Plt./130
See application file for complete search history.

*Primary Examiner* — Annette Para

(57) ABSTRACT

A new and distinct variety of rose with long lasting, novel lavender flowers, and attractive foliage with very good disease resistance. It exhibits upright to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORfre0005'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2001. The crossing was between an un-named seedling, the seed parent, and another un-named seedling, the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORfre0005'.

SUMMARY OF THE INVENTION

The new rose plant may be distinguished from its seed parent, an un-named seedling, by the following combination of characteristics:

1. 'KORfre0005' has lavender flowers, whereas the un-named seedling has light pink flowers.
2. 'KORfre0005' has medium flowers, whereas the un-named seedling has small flowers.

The new rose plant may be distinguished from its pollen parent, an un-named seedling, by the following combination of characteristics:

1. 'KORfre0005' has lavender flowers, whereas the un-named seedling has pale lavender-blue flowers.
2. 'KORfre0005' has an upright to bushy growth habit, whereas the un-named seedling has spreading growth habit.

The objective of the hybridization was to create a new and distinct rose plant with unique qualities, such as:

1. Uniform growth and flowering;
2. Abundant attractive, recurrent flowers which can be used in the commercial cut flower trade;
3. Attractive and abundant foliage; and
4. Resistance to diseases encountered in commercial flower culture.

This combination of qualities is not present in prior rose cultivars known to the inventor. These objectives have been substantially achieved and in that distinguish 'KORfre0005' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORfre0005' was selected in 2007 from the seedling beds to be asexually propagated for further evaluation. The first asexual propagation of 'KORfre0005' was done by budding in 2007 at the inventor's nursery in Offenseth-Sparrieshoop, Germany.

These initial and other subsequent propagations conducted in controlled environments demonstrate that 'KORfre0005' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORfre0005'.

DETAILED BOTANICAL DESCRIPTION

The following is a description of 'KORfre0005', as observed growing in July 2014 in a nursery in Jackson County, Oreg. on plants of 10 months of age. Color references are made using The Royal Horticultural Society (London, England) Colour Chart, 2001 except where common terms of color are used.

For a comparison, several physical characteristics of the rose variety 'KORfriedhar', a rose variety from the same inventor described and illustrated in U.S. Plant Pat. No. 23,555 and issued on Apr. 23, 2013 are compared to 'KORfre0005' in Chart 1.

CHART 1

| Characteristic | 'KORfre0005' | 'KORfriedhar' |
|---|---|---|
| Average plant height. | 120 cm. | 80 cm. |
| Flower duration on the plant. | 14 days. | 3 to 5 days. |
| Number of pistils. | Approximately 80. | Approximately 10 to 12. |

Parents:

*Seed parent*.—An un-named seedling.

*Pollen parent*.—An un-named seedling.

Classification:

*Botanical classification*.—*Rosa hybrida* 'KORfre0005'.

*Commercial classification*.—Grandiflora rose.

FLOWER AND FLOWER BUD

Blooming habit: Recurrent.

Flower bud:

*Size*.—Upon opening, 25 mm in length from base of receptacle to distal end of bud and 23 mm diameter at its widest point.

*Bud form*.—Short. Globular.

*Bud color*.—As sepals first unfold, bud color is Violet Group 85D to 85C. When ¼ open, the upper surface of petals is Violet Group 85D, and the lower surface is Violet Group 85D. Guard Petals are Violet Group 85C with intonations of Yellow-Green Group 146C and occasionally Greyed-Red Group 181C.

*Sepals*.—Color: Upper surface: Yellow-Green Group 146D, with slight intonations of Greyed-Red Group 184D along the midlrib. Lower surface: Yellow-Green Group 146C. Size: Average 15 mm (l)×8 mm (w). Shape: Very weak foliaceous appendages on 3 of the five sepals. Apex: Apiculate. Base: Flat at union with receptacle. Quantity: Five. Surface texture: Upper side: Pubescent. Lower surface: Smooth. Margins: Lightly pubescent with moderate numbers of stipitate glands. Stipitate glands: Moderate.

Flower bloom:

*Fragrance*.—Light anise fragrance.

*Duration*.—On the plant 14 days. As a cut flower, 10 days. Senesced petals drop away cleanly.

*Size*.—Medium for a Grandiflora rose. When open, the average flower diameter is 75 mm and the average flower height is 40 mm.

*Form*.—Shape of flower when viewed from the side: Upon opening, upper part: Flat. Upon opening, lower part: Flattened convex. Open flower, upper part: Flattened convex. Open flower, lower part: Flattened convex.

*Color*.—Upon opening, petals: Outermost petals: Outer Side: Violet Group 84C. Inner Side: Violet-Blue Group 91C. Innermost petals: Outer Side: Violet-Blue Group 91D. Inner Side: Violet-Blue Group 91C. No distinctive coloration at petal base observed. After opening, petals: Outermost petals: Outer Side: Violet-Blue Group 92C. Inner Side: Violet-Blue Group 92D. Innermost petals: Outer Side: Violet Group 85D. Inner Side: Violet Group 92C. No distinctive coloration at petal base observed.

General tonality: On open flower Violet Group 85C. No change in the general tonality at the end of the 8th day. Afterwards, general tonality is White Group N155A.

Petals:

*Petal count*.—Very double.

*Average range*.—Approximately 70 petals under normal conditions.

*Petal reflex*.—Petals reflex somewhat.

*Petal margin*.—Entire, moderately undulate.

*Petal shape*.—Obovate. Apex: Obtuse, ocasionally mucronate. Base: Cuneate.

*Petal size*.—30 to 35 mm (l)×25 to 35 mm (w).

*Petal arrangement*.—Not formal.

*Texture*.—Smooth.

Petaloids:

*Petaloid count*.—Average of 1 to 3 per flower.

*Petaloid size*.—10 to 12 mm (l)×4 to 8 mm (w).

*Petaloid color*.—Inner side: Violet Group 86D. Outer side: Violet Group N88D.

*Petaloid texture*.—Smooth.

*Margins*.—Highly irregular, with many margins undulated and indented.

*Petaloid shape*.—Most commonly obovate. Apex: Obtuse. Base: Attenuate.

Reproductive organs:

*Pistils*.—Abundant. Approximately 80 present. Stigmas: Location: Slightly inferior in position to anthers. Color: Greyed-Yellow Group 160C. Styles: Length: About 5 to 8 mm long. Color: Greyed-Yellow Group 160D.

*Stamens*.—Approximately 60 on average and regularly arranged. Anthers:

*Size*.—Average 1 mm (l)×2 mm (w). Pollen: Generally present. Color: Yellow Group 4C. Filaments: Color: Yellow Group 4C. Length: 11 mm.

*Receptacle*.—Surface: Smooth. Color: Yellow-Green Group. Shape: Funnel-shaped. Texture: Smooth, with occasional stipitate glands. Size: 10 mm (h)×9 mm (w).

*Pedicel*.—Surface: Glabrous. Length: 30 to 50 mm average length. Diameter: 2 to 4 mm average diameter. Color: Yellow-Green Group 144C. Strength: Strong. Texture: Smooth. Borne: Multiple flower buds per stem, generally 3 to 4, with occasional single blooms. Flowers held upright.

*Peduncle*.—Surface: Glabrous. Length: 40 to 80 mm average length. Diameter: 3 to 4 mm average diameter. Color: Yellow-Green Group 144C. Strength:

Strong. Borne: Multiple flower buds per stem, generally 3 to 4, with occasional single blooms. Flowers held upright.

THE PLANT

Growth: Moderately vigorous.

Plant habit: Upright to bushy. When grown as a field plant, the average plant height is 120 cm and the average plant width is 90 cm.

Stems:

*Stem color*.—Young wood: Yellow-Green Group 144C. Older wood: 144B.

*Stem surface texture*.—Young wood: Smooth. Older wood: Smooth.

Prickles: Present.

*Incidence*.—Average of 5 per each 10 cm of stem.

*Size*.—Average length: 1 to 2 mm.

*Color*.—Immature prickles: Greyed-Purple 184C. Mature prickles: Greyed-Brown N199A.

*Shape*.—Flat.

Leaves: Normally 5 leaflets on normal leaves in middle of the stem.

*Venation pattern*.—Pyramidal net pattern.

*Leaf size*.—140 mm (l)×120 mm (w).

*Abundance*.—Average.

Leaflets:

*Size*.—Average size of the terminal leaflet is 70 mm (l)×55 mm (w).

*Shape*.—Elliptic. Base: Obtuse. Apex: Broadly obtuse.

*Margins*.—Serrated.

*Surface*.—Semi-glossy.

*Texture*.—Upper side of leaflet: Leathery. Under side of leaflet: Leathery.

*Color, mature foliage*.—Upper Leaflet Surface: Green Group 137C. Lower Leaflet Surface: Yellow-Green Group 147B.

*Color, juvenile foliage*.—Upper Leaflet Surface: Yellow-Green Group 147A. Lower Leaflet Surface: Yellow-Green Group 147B.

*Anthocyanin intonation*.—Greyed-Purple Group 187B. Location: Upper and lower surfaces of juvenile foliage.

*Arrangement*.—Odd pinnate.

*Venation*.—Reticulate.

Stipules:

*Size*.—20 mm (l)×5 mm (w).

*Stipule color*.—Yellow-Green Group 144B.

*Stipitate glands*.—Limited numbers of stipitate glands along margins and on upper surface of stipule.

*Margins*.—Limited numbers of stipitate glands present.

*Texture*.—Smooth.

*Shape*.—Apex: Apiculate. Base: Winged. Fused to the petiole.

Petiole:

*Length*.—Average 15 mm.

*Diameter*.—Average 2 mm.

*Petiole color*.—Yellow-Green Group 144B. Underneath: Yellow-Green Group 144B.

*Margins*.—With stipitate glands.

*Anthocyanin*.—None observed.

*Prickles*.—A few small prickles underneath.

*Stipitate glands*.—Limited numbers of stipitate glands regularly spaced on upper surface.

*Texture*.—Smooth.

Petiole rachis:

*Length*.—Average 15 mm.

*Diameter*.—Average 1.5 mm.

*Color*.—Yellow-Green Group 144B.

*Margins*.—Stipitate glands present.

*Prickles*.—Lacking.

*Stipitate glands*.—Abundant numbers of stipitate glands on upper margins and lower surface.

Hips/seed formation: None observed.

Winter hardiness: To date, the variety has been grown successfully in Zone 6.

Disease resistance: Very good resistance to powdery mildew (*Sphaerotheca pannosa*), blackspot (*Diplocarpon rosae*), rust (*Phragmidium* sp.), and botrytis (*Botrytis cinerea*) diseases under normal growing conditions in Jackson County, Oreg.

I claim:

1. A new and distinct variety of rose plant, as described and illustrated herein.

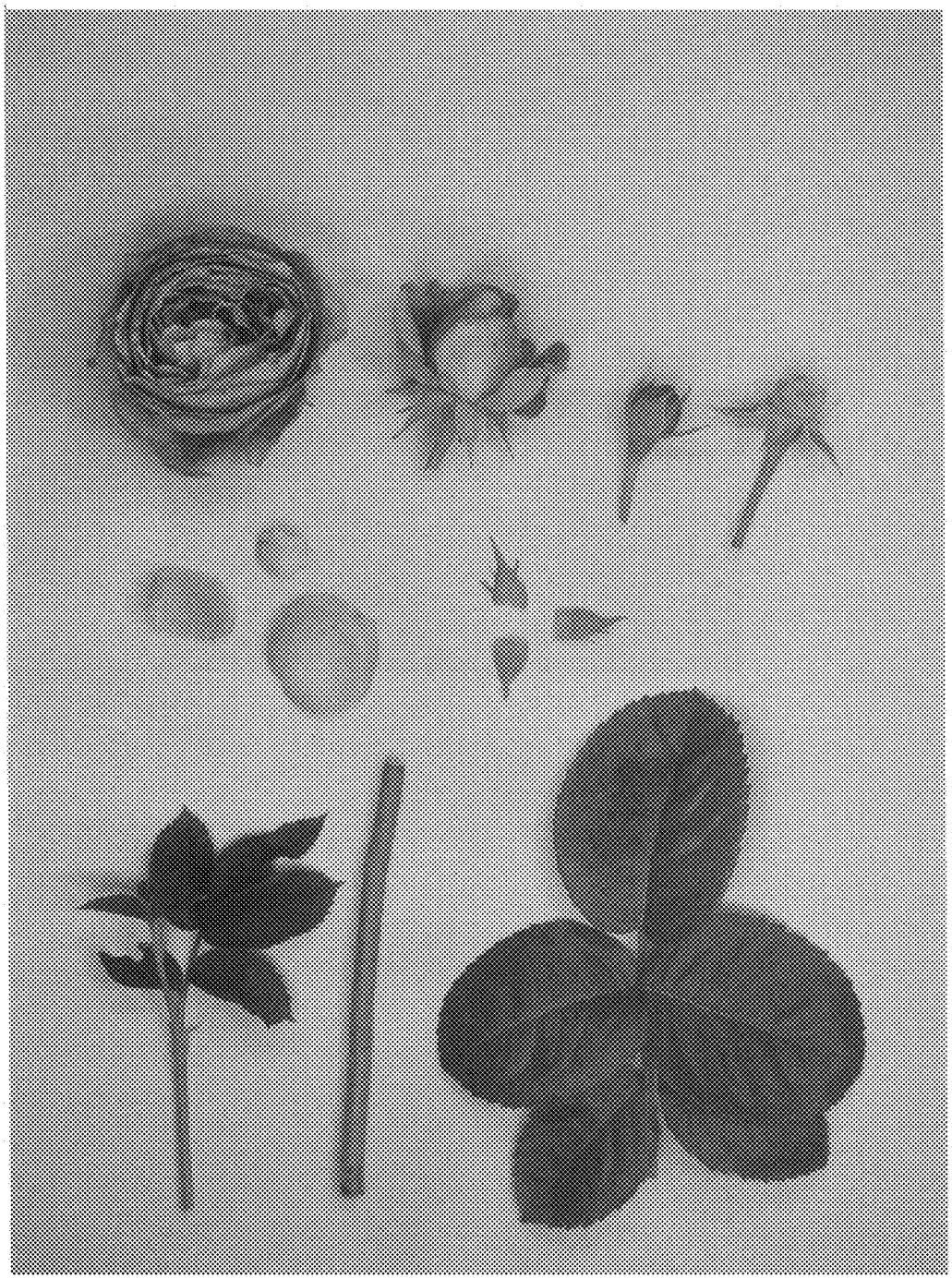

* * * * *